United States Patent [19]
Lary

[11] Patent Number: 5,649,941
[45] Date of Patent: Jul. 22, 1997

[54] IMPROVED VASCULAR INCISOR/DILATOR

[75] Inventor: Banning Gray Lary, Miami, Fla.

[73] Assignee: Interventional Technologies Inc., San Diego, Calif.

[21] Appl. No.: 576,194

[22] Filed: Dec. 20, 1995

Related U.S. Application Data

[63] Continuation-in-part of Ser. No. 370,893, Jan. 10, 1995, abandoned.

[51] Int. Cl.⁶ .................................................. A61B 17/32
[52] U.S. Cl. .......... 606/159; 606/170; 606/171; 606/180; 604/22
[58] Field of Search ................. 606/1, 159, 170, 606/171, 180, 191; 604/22, 96; 128/898

[56] References Cited

U.S. PATENT DOCUMENTS

| | | |
|---|---|---|
| 2,729,210 | 1/1956 | Spencer. |
| 2,749,909 | 6/1956 | Ullery et al.. |
| 4,273,128 | 6/1981 | Lary. |
| 4,650,466 | 3/1987 | Luther. |
| 4,723,549 | 2/1988 | Wholey et al.. |
| 4,867,156 | 9/1989 | Stack et al.. |
| 5,009,659 | 4/1991 | Hamlin. |
| 5,053,044 | 10/1991 | Mueller et al.. |
| 5,100,426 | 3/1992 | Nixon ................................. 606/159 |
| 5,196,024 | 3/1993 | Barath ................................. 606/159 |
| 5,224,949 | 7/1993 | Gomringer et al.. |
| 5,372,601 | 12/1994 | Lary. |
| 5,395,311 | 3/1995 | Andrews. |

FOREIGN PATENT DOCUMENTS

| | | |
|---|---|---|
| 0 401 158 | 12/1990 | European Pat. Off.. |
| 0 419 154 A1 | 3/1991 | European Pat. Off.. |
| 565796 | 10/1993 | European Pat. Off.. |
| 0 619 986 A1 | 10/1994 | European Pat. Off.. |
| 3519626 | 12/1986 | Germany. |
| 3732236 | 12/1988 | Germany. |
| 1516120 | 10/1989 | U.S.S.R.. |
| WO 90/07909 | 7/1990 | WIPO. |

*Primary Examiner*—Michael Buiz
*Assistant Examiner*—William Lewis
*Attorney, Agent, or Firm*—Nydegger & Associates

[57] ABSTRACT

A device and method for clearing a stenosis in a vessel of a patient requires a catheter having a rigid, cone-shaped probe at its distal end. The probe has a distally diminishing taper and also has a plurality of blades which are mounted on the probe and longitudinally aligned with the catheter. The probe is formed to include a series of grooves which span the length of the probe. Advancement of the probe through the vessel to the stenosis can be accomplished either over a prepositioned guidewire or through a prepositioned guide catheter. At the stenosis, the probe with mounted blades are reciprocally moved back and forth across the stenosis to incise and dilate the stenosis and, thus, clear the stenosis. Blood flow is maintained within the vessel by the grooves formed in the surface of the probe. Movement of the probe across the stenosis can be facilitated by selectively activating a rigidizer which is located on the catheter immediately proximal to the probe. Additionally, a balloon can be mounted on the catheter proximal the dilation probe and selectively inflated at the stenosis after the stenosis has been incised and dilated.

20 Claims, 3 Drawing Sheets

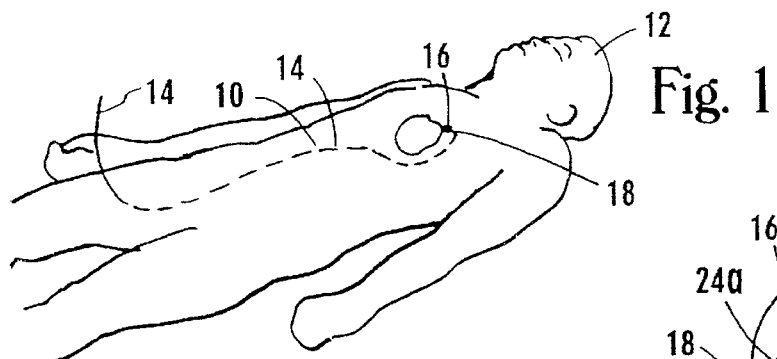
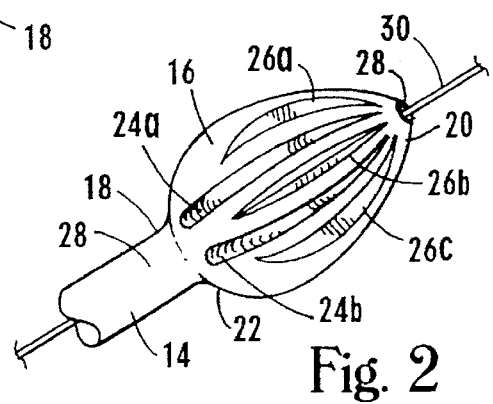
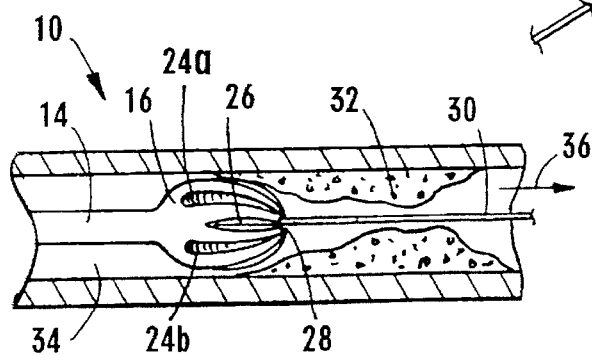
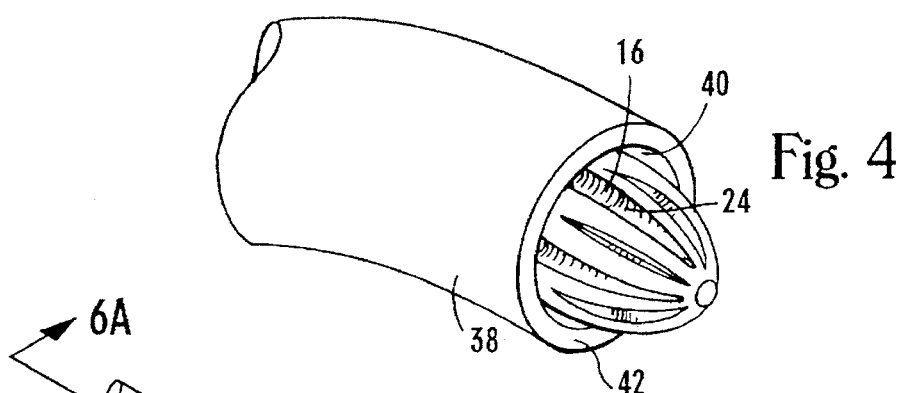
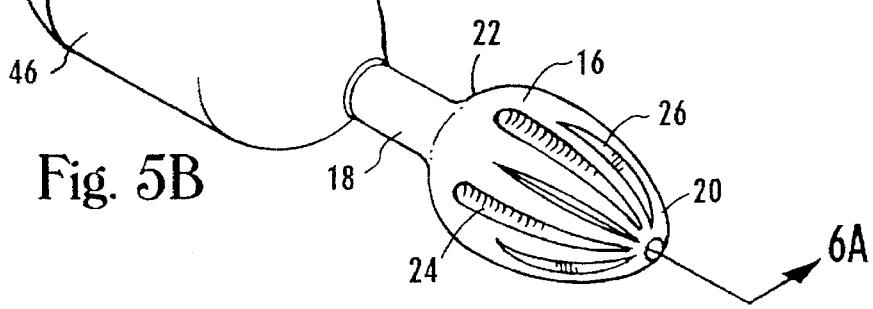

IMPROVED VASCULAR INCISOR/DILATOR

This is a continuation-in-part patent application of U.S. patent application Ser. No. 08/370,893, filed on Jan. 10, 1995, and entitled "Vascular Incisor/Dilator, now abandoned."

FIELD OF THE INVENTION

The present invention pertains generally to surgical devices and procedures. More particularly, the present invention pertains to devices and methods for clearing a stenosis from the artery of a patient. The present invention is particularly, but not exclusively useful, for both incising and subsequently dilating a vessel to clear an obstruction or stenosis from the vessel.

BACKGROUND OF THE INVENTION

Many medical complications are created by the total or even partial blockage of blood vessels of the body. The primary cause of these complications is, of course, the reduction or cessation of blood flow through the blocked vessels to the particular biological tissue which is serviced by the vessel. Most commonly, a blockage, or stenosis, is formed in an artery as a result of plaque build-up in the artery. Further, it is not uncommon for several stenoses to occur sequentially in a single artery or to develop near one another in branches of a common central artery.

Traditionally, removal of stenotic material from the arterial vessels of a patient has required direct surgical access to the involved vessel. For example, in a typical coronary by-pass procedure, the surgeon will actually replace the stenotic segment of the involved artery with a graft artery taken from another part of the patient's body. Generally, although techniques of this type may be highly effective, and even life-saving, they are costly in terms of patient trauma.

As an alternative to methods requiring direct access to the involved vessel, several methods, or procedures, have been developed wherein access to the stenosis is achieved indirectly through a peripheral artery. Many of these methods involve insertion of a dilation device into the peripheral artery. After insertion, the device is advanced through the peripheral artery until it reaches the site of the stenosis. The device is then manipulated to dilate the stenosis thereby improving the flow of blood through the stenotic segment.

An example of a dilation-type procedure, which is known as balloon angioplasty, is disclosed in U.S. Pat. No. Re. 33,561 which issued to Levy for an invention entitled "BALLOON AND MANUFACTURE THEREOF." As taught by Levy, a deflated dilatation balloon is inserted into the vessel and is placed across the stenosis. Once the balloon is properly positioned, it is then inflated to dilate the artery and thereby clear the stenosis.

Recent studies have indicated that for procedures wherein a stenosis is to be dilated, such as for an angioplasty procedure, the efficacy of the dilatation is enhanced by first incising the material which is creating the stenosis. With this knowledge, several devices for clearing blocked arteries have been proposed. For example, U.S. Pat. No. 4,273,128 which issued to Lary for an invention entitled "CORONARY CUTTING AND DILATING INSTRUMENT" discloses a surgical instrument which both incises and dilates a stenosis. As another example, U.S. Pat. No. 5,209,799 which issued to Vigil for an invention entitled "METHOD FOR MANUFACTURING A FOLDING BALLOON CATHETER" discloses a folding angioplasty balloon with attached atherotomes.

While angioplasty and by-pass surgery procedures, as disclosed above, are efficacious for their intended purposes, it happens that less aggressive methods may also be appropriate and just as effective for removing or clearing a stenosis from the vessel of a patient. Moreover, less aggressive methods may be preferable. This is particularly so where shorter, and perhaps more numerous, stenoses are involved. It is also the case that both angioplasty and by-pass surgery procedures necessarily result in some cessation of blood flow within the involved vessel during the course of the procedure. It happens that less aggressive methods may effectively remove stenotic segments while still maintaining blood flow within the involved vessel.

In light of the above it is an object of the present invention to provide a device and method for incising and dilating a stenosis in a vessel of a patient which is particularly efficacious for shorter stenotic blockages in the vessel. Another object of the present invention is to provide a device and method for incising and dilating a stenosis in a vessel of a patient which can be used with either direct or indirect access to the stenosis. Still another object of the present invention is to provide a device and method for incising and dilating a stenosis in a vessel of a patient which can be effectively used to augment a more aggressive procedure such as either angioplasty, athrectomy or by-pass surgery. Yet another object is to provide a device which can cut and dilate numerous areas of stenoses in a single vessel and which is replaceable with a smaller identical apparatus which will pass through proximal stenoses that have been previously removed to clear stenoses in the smaller distal position of the same vessel. Yet another object of the present invention is to provide a device for incising and dilating a stenosis in a vessel of a patient which maintains adequate blood flow within the involved vessel during the process of incision and dilation. Yet another object of the present invention is to provide a device for incising and dilating a stenosis in a vessel of a patient which is relatively simple to manufacture, easy to use, and comparatively cost effective.

SUMMARY OF THE INVENTION

A device and method for incising and dilating a stenosis in a vessel of a patient includes a catheter and a dilation probe which is fixedly attached to the distal end of the catheter. The dilation probe is generally cone-shaped with smooth transitions and is tapered with diminishing cross section in the distal direction. A series of grooves are formed in the surface of the cone-shaped probe. The grooves are aligned substantially in parallel with the longitudinal axis of the probe and catheter and extend over the length of the probe. Additionally, a plurality of atheretomes, or elongated blades, are mounted on the dilation probe and are aligned longitudinally with the catheter.

In the operation of the device of the present invention, the dilation probe is advanced through a vessel of the patient to the stenosis. At the stenosis, the dilation probe may be reciprocally moved back and forth through the stenosis, as necessary, to incise the stenosis with the blades and to dilate the stenosis with the tapered portion of the dilation probe. As the probe is advanced through the stenosis, the grooves formed in the surface of the probe provides a means for fluid, such as blood to flow past the probe. In this fashion, blood flow is maintained in the vessel during the incision and dilation process.

Several embodiments of the present invention are possible for advancing the dilation probe to the stenosis. One such embodiment requires a contiguous lumen be formed through the catheter and the dilation probe. A guidewire can then be prepositioned in the vessel at least up to the stenosis and, with the guidewire inserted into the contiguous lumen, the combination of catheter and dilation probe can be advanced to the stenosis. In another embodiment of the present invention, a guide catheter is provided which has a lumen for receiving the combination of catheter and dilation probe therethrough. For this embodiment, the guide catheter is prepositioned in the vessel of the patient and the dilation probe is advanced through the lumen of the guide catheter to the stenosis.

The catheter can also include a dilatation balloon. For this embodiment of the present invention, a selectively inflatable balloon is incorporated into the catheter at a location on the catheter that is proximal to the dilation probe. In the operation of this embodiment, after the dilation probe has been advanced through the stenosis to incise and initially dilate the stenosis, the dilatation balloon is positioned across the stenosis and inflated for further dilatation of the stenosis.

Operation of the catheter for advancing the dilation probe to the stenosis and for moving the dilation probe through the stenosis can be facilitated with the incorporation of a rigidizer in the catheter. For purposes of the present invention, the rigidizer is located on the catheter immediately proximal to the dilation probe. The rigidizer includes a deformable cavity which is formed into the catheter to confine loosely packed granules, and a suction device for evacuating air from the cavity to tightly pack the granules together. Thus, with some air in the rigidizer cavity, the loosely packed granules allow for flexibility of the catheter during advancement of the dilation probe to the stenosis. On the other hand, upon evacuation of air from the rigidizer cavity, the granules become tightly packed and provide a stiff rigid structure for movement of the dilation probe through the stenosis. In addition to improving the operability of the device for cleaning a stenosis, this feature also permits the apparatus to maneuver effectively through branches and angles of the blood vessels.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 1 is a perspective view of a patient being operated on, with the device of the present invention being indirectly inserted through a peripheral vessel of the patient to the stenosis site;

FIG. 2 is a perspective view of the dilation probe of the device of the present invention shown in cooperation with a guidewire;

FIG. 3 is an exemplary view of the dilation probe of the device of the present invention at a stenosis in a vessel of the patient;

FIG. 4 is a perspective view of the device of the present invention being used with a guide catheter;

FIG. 5B is a perspective view of the device of the present invention, as seen in FIG. 5A, with the dilatation balloon inflated;

DESCRIPTION OF THE PREFERRED EMBODIMENTS

Figure 5A:
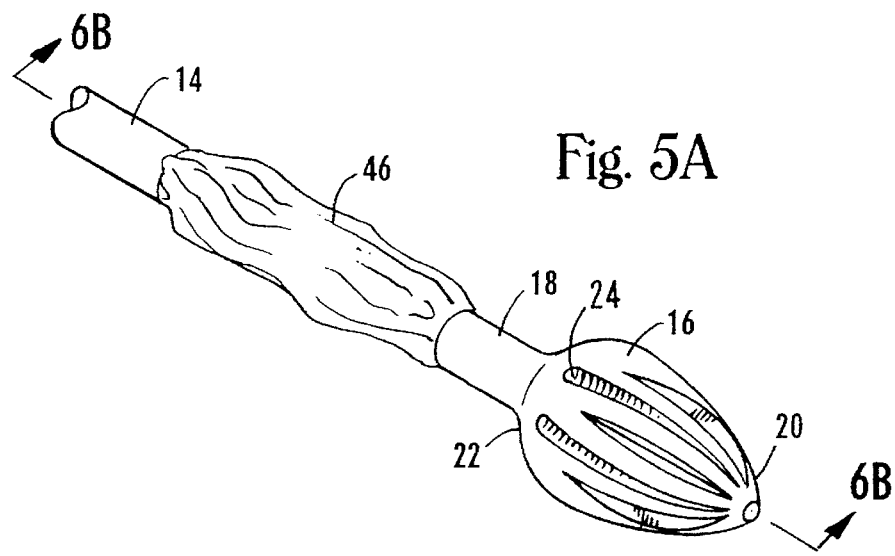
FIG. 5A is a perspective view of an alternate embodiment of the device of the present invention which incorporates a dilatation balloon, with the balloon deflated.

Referring initially to FIG. 1 the device for incising and dilating a stenosis in a patient is shown and generally designated 10. As shown, the device 10 is shown inserted into a peripheral artery of the patient 12. The device 10 generally includes a catheter 14 and a rigid dilation probe 16. As indicated in FIG. 1, the dilation probe 16 is fixedly attached to the distal end 18 of catheter 14 for movement therewith.

As perhaps best seen in FIG. 2, the dilation probe 16 of the device 10 has a distal end 20 and a proximal end 22. Between distal end 20 and proximal end 22, probe 16 is generally cone-shaped and is tapered with a diminishing cross-section in the distal direction. Further, dilation probe 16 has smooth transitions so as not to present rough or angular edges which could become caught or snagged on irregularities in the vessel. A series of grooves 24, of which the grooves 24a and 24b are exemplary, are formed in the surface of the dilation probe 16. The grooves 24 are aligned to substantially parallel the longitudinal axis of the catheter 14 and probe 16 and each groove 24 has an overall length which spans the surface of the probe 16 between distal end 20 and proximal end 22.

Additionally, and importantly, dilation probe 16 includes a plurality of blades 26, of which the blades 26 a–c are exemplary. More specifically, the blades 26 are mounted on the tapered portion of dilation probe 16 and are aligned with a longitudinal axis that is defined by an extended catheter 14. FIG. 2 also shows that both the catheter 14 and dilation probe 16 are formed with a contiguous lumen 28 which extends the entire length of the device 10. As will be appreciated by the skilled artisan, lumen 28 is dimensioned to receive a guidewire 30 therethrough to facilitate proper placement of the dilation probe 16 in the vessel of the patient 12.

As indicated in FIG. 3, in the operation of the device 10, the guidewire 30 is prepositioned in the patient 12. The dilation probe 16 and catheter 14 are then positioned over the guidewire 30. This is done by inserting guidewire 30 into lumen 28 of the device 10. Dilation probe 16 is then advanced along the guidewire 30 and into contact with the stenosis 32 which is blocking blood flow through the vessel of the patient 12. Typically, and as shown in FIG. 3, a stenosis 32 occurs due to the build-up of plaque on the wall 34 of the vessel. To clear the stenosis 32, the effect of the build-up must be removed or otherwise eliminated. With the device 10 of the present invention this is accomplished by advancing the dilation probe 16 along guidewire 30 in the direction of arrow 36 and through the stenosis 32. As this is done, the blade 26 of dilation probe 16 first incise the stenosis 32. Additional advancement of dilation probe 16 causes the dilation probe 16, itself, to urge against the stenosis 32. This causes the stenosis to dilate as dilation probe 16 is advanced. If necessary, dilation probe 16 can be moved back and forth across the stenosis 32 with multiple passes.

As the dilation probe 16 moves through the stenosis 32, grooves 24 provide a pathway for fluid to flow between distal end 20 and proximal end 22 of the probe 16. In this fashion fluid flow is maintained within the vessel during incision and dilation of the stenosis 32.

As an alternative for advancing dilation probe 16 to the site of the stenosis 32, rather than using a guidewire 30, a guide catheter 38 can be employed. As shown in FIG. 4, guide catheter 38 is formed with a lumen 40 which is of sufficient size to receive the dilation probe 16 and catheter 14 therethrough. In the operation of this embodiment of the present invention, the guide catheter 38 is prepositioned in the vessel of patient 12 with its distal end 42 located just proximal to the stenosis 32. dilation probe 16 is then advanced through lumen 40 of guide catheter 38 and into contact with stenosis 32. Again, as disclosed above, stenosis 32 is incised and dilated as dilation probe 16 is further advanced distally from distal end 42 of guide catheter 38 through stenosis 32. Also, as before, dilation probe 16 can be given a back and forth motion across the stenosis 32, if required.

Figure 6A:
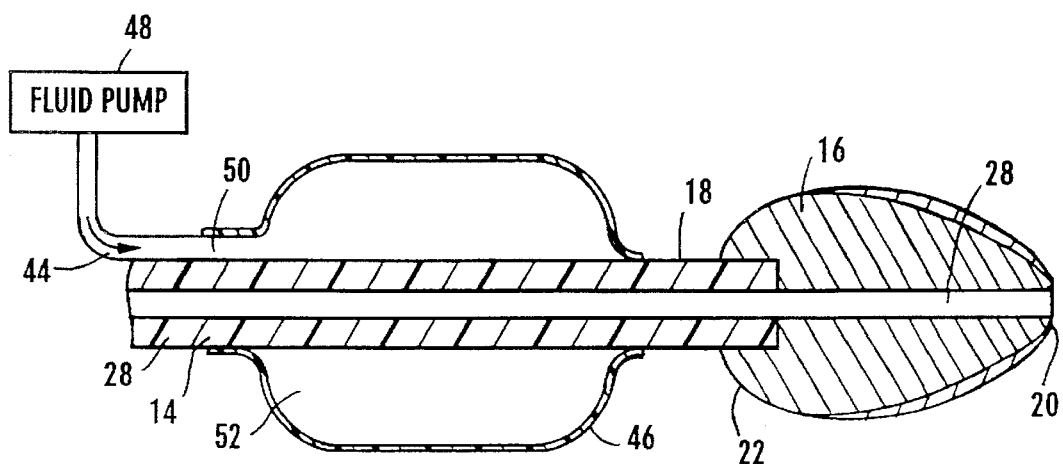
FIG. 6A is a cross sectional view of the device of the present invention as seen along the line 6A—6A in FIG. 5B.
Figure 6B:
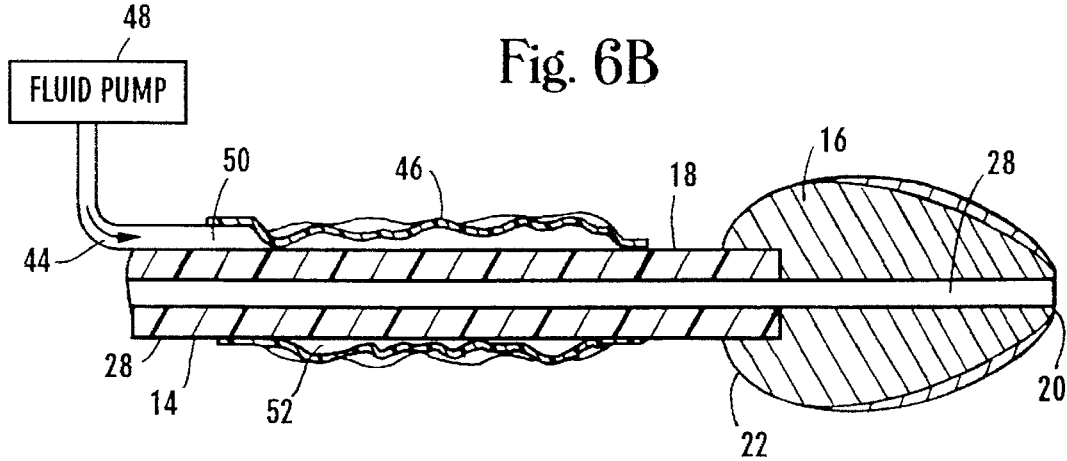
FIG. 6B is a cross sectional view of the device of the present invention as seen along the line 6B—6B in FIG. 5A.

FIGS. 5A, 5B, 6A–6B illustrate an alternate embodiment for the device 10 which additionally incorporates a dilatation balloon 46. More specifically, as shown, the dilatation balloon 46 is positioned on the catheter 14 at a location proximal to dilation probe 16. As best seen in FIG. 6A, a fluid pump 48 which is located off the proximal end of catheter 14, and which remains extracorporeal, is connected in fluid communication with a passageway 50 that is formed by a tube 44 which is coaxial with catheter 14 and which is attached in a fluid communication with the proximal end of balloon 46. Accordingly, by selectively operating fluid pump 48, fluid can be introduced into the potential chamber 52 established by balloon 46 to change device 10 from the configuration shown in FIGS. 5A and 6B, wherein balloon 46 is deflated, into the configuration shown in FIGS. 5B and 6A wherein balloon 46 is inflated. In the operation of this alternate embodiment of device 10, dilation probe 16 can be advanced to a stenosis 32 using either a guidewire 30 or a guide catheter 38 as disclosed above. Once dilation probe 16 has been advanced through stenosis 32 to incise stenosis 32 with blades 26 and dilate stenosis 32, a deflated balloon 46 can be positioned across the stenosis 32. Inflation of balloon 46 at that point will then provide further action for dilating stenosis 32. When desired, balloon 46 can be deflated and the device 10 removed from the vessel of patient 12.

Figure 7A:
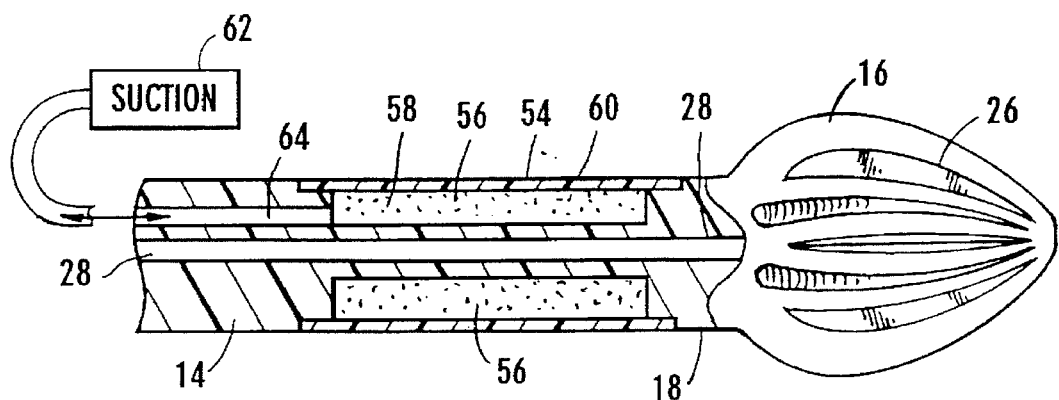
FIG. 7A is a cross sectional view of another embodiment of the device of the present invention which incorporates a rigidizing structure, as this embodiment would be seen along the line 6A—6A in FIG. 5B, with the rigidizing structure in a flexible configuration.
Figure 7B:
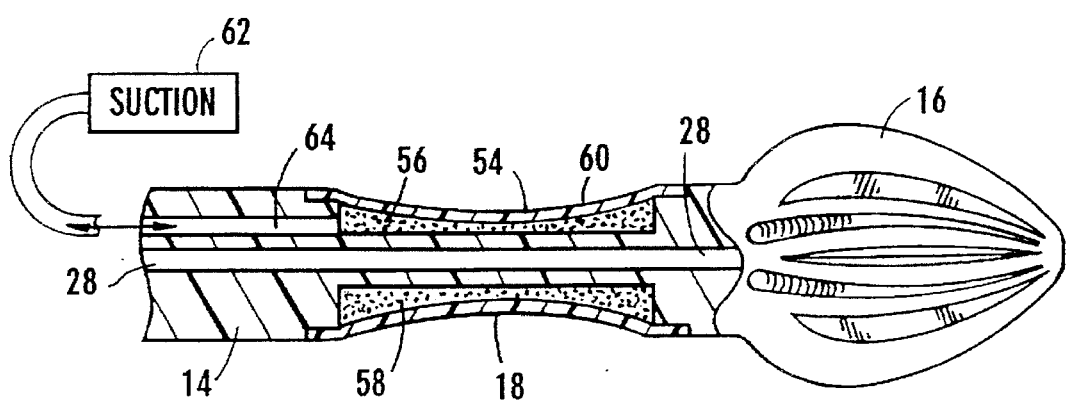
FIG. 7B is a cross sectional view of the embodiment of the device of the present invention shown in FIG. 7A with the rigidizing structure in a rigid configuration.

Yet another embodiment for the device 10 of the present invention is shown in FIGS. 7A and 7B. This particular embodiment incorporates a rigidizer 54 which allows the distal end 18 of catheter 14 to be selectively either limp or rigid. More specifically, rigidizer 54 includes a chamber 56 that is formed into the shaft of catheter 14 and which is loosely filled with biocompatible granules 58 (such as particles of dextran). More specifically, the external wall of the chamber 56 can include a sleeve 60 which is made of a relatively flexible material. The sleeve 60 is attached to catheter 14 to cover chamber 56. It will be appreciated, that catheter 14 is, itself, made of a somewhat flexible material. Sleeve 60, however, can be even more flexible or even deformable. FIG. 7A also shows that a suction pump 62 is located off the proximal end of catheter 14 and that the suction pump 62 is in fluid communication with a lumen 64 which is formed in catheter 14. Lumen 64, in turn, is in fluid communication with chamber 56.

As intended for the present invention, when the rigidizer 54 is deactivated, the granules 58 are loosely held in chamber 56. Consequently, with a deactivated rigidizer 54 the dilation probe 16 is effectively held by only the flexible material of catheter 14. This allows the distal end 18 of catheter 14 and the dilation probe 16 to be limp and therefore more maneuverable in their advancement toward a stenosis 32. This advancement may, of course, be either over a guidewire 30 or through a guide catheter 38. On the other hand, such limpness most likely will not be suitable for a further advancement of dilation probe 16 through the stenosis 32. To do this, the rigidizer 54 needs to be activated.

Activation of rigidizer 54 is accomplished by pulling a vacuum with the suction pump 62 to evacuate air or fluid from the chamber 56. Due to the flexibility of sleeve 60, as air or fluid is evacuated from chamber 56 the sleeve 60 will collapse under the action of the suction pump 62. This, in turn, will cause granules 58 in chamber 56 to be compressed onto each other forming a rigid structure. The result is that portion of catheter 14 where chamber 56 is located becomes stiff and rigid, holding whatever shape the catheter was in when the tube was evacuated. This stiffness then allows the user to advance dilation probe 16 through a stenosis 32 with a reduced risk of any buckling or bending of the distal end 18 of catheter 14.

Although the device 10 has been described and disclosed for cooperation with a guidewire 30 or guide catheter 38, it is to be appreciated that the device 10 can be operated without either the guidewire 30 or guide catheter 38. This will particularly be the case when direct access to a stenosis is possible. Without a guidewire 30 or guide catheter 38, the catheter 14 must, itself, have sufficient controllability and steerability to advance the dilation probe 16 to a stenosis.

While the particular device for incising and dilating a stenosis in a vessel of a patient as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

I claim:

1. A device for clearing a stenosis in a vessel of a patient without compromising fluid flow in said vessel, said device comprising:

a catheter having a distal end;

a rigid dilation probe, said dilation probe having a proximal end attached to said distal end of said catheter, said dilation probe also having a tapered distal end, said dilation probe formed with a plurality of grooves, each said groove extending between said distal end of said dilation probe and said proximal end of said dilation probe; and a plurality of blades attached to project radially from said dilation probe.

2. A device as recited in claim 1 further comprising guide means for advancing said dilation probe through said vessel to said stenosis.

3. A device as recited in claim 2 wherein said guide means is a guidewire, said guidewire having a distal end prepositionable in the vessel, said guidewire also having a proximal end insertable through a contiguous lumen formed in said dilation probe, said dilation probe advancable over said guidewire to guide said dilation probe to said stenosis.

4. A device as recited in claim 2 wherein said guide means is a guide catheter, said guide catheter being prepositionable in said vessel, said guide catheter formed with a lumen for receiving said dilation probe and said catheter to guide said dilation probe to the stenosis.

5. A device as recited in claim 2 wherein said dilation probe is substantially conical in shape.

6. A device as recited in claim 2 wherein said dilation probe is substantially ellipsoidal in shape.

7. A device as recited in claim 2 wherein said dilation probe and said catheter define a longitudinal axis and wherein said blades are aligned to substantially parallel said longitudinal axis.

8. A device as recited in claim 2 further comprising a selectively inflatable balloon mounted on said catheter proximal to said dilation probe.

9. A device as recited in claim 2 further comprising means for rigidizing a portion of said catheter to facilitate movement of said dilation probe through the stenosis.

10. A device for clearing a stenosis in a vessel of a patient without compromising fluid flow in said vessel, said device comprising:

a dilation probe for dilating said stenosis, said dilation probe having a distal end and a proximal end and being formed with a plurality of fluid channels for establishing fluid communication between said distal end and said proximal end thereof;

a plurality of blades attached to said dilation probe, said blades projecting radially from said dilation probe for incising said stenosis;

means for advancing said dilation probe through said vessel to said stenosis; and a catheter having a distal end, said distal end of said catheter being fixedly attached to said dilation probe for moving said dilation probe through said vessel and said stenosis for dilating and incising said stenosis.

11. A device as recited in claim 10 wherein said catheter and said dilation probe are formed with a contiguous lumen and said means for advancing is a guidewire, said guidewire being prepositionable in the vessel and insertable through said lumen to guide said dilation probe to the stenosis.

12. A device as recited in claim 10 wherein said means for advancing is a guide catheter, said guide catheter being prepositionable in the vessel and formed with a lumen for receiving said dilation probe and said catheter therethrough to advance said dilation probe to the stenosis.

13. A device as recited in claim 10 wherein said dilation probe is substantially cone-shaped with a tapered portion having a diminishing cross sectional area in the distal direction, and wherein said catheter defines a longitudinal axis and said blades are aligned longitudinally on said dilation probe.

14. A device as recited in claim 10 further comprising a selectively inflatable balloon mounted on said catheter proximal to said dilation probe.

15. A device as recited in claim 10 further comprising means for rigidizing a portion of said catheter proximal to said dilation probe.

16. A method for clearing a stenosis in a vessel of a patient without compromising fluid flow in said vessel which comprises the steps of:

advancing a device to the stenosis through the vessel, said device comprising a catheter having a distal end, a rigid dilation probe, said dilation probe having a proximal end attached to said distal end of said catheter, said dilation probe also having a tapered distal end, said dilation probe formed with a plurality of grooves, each said groove extending between said distal end of said dilation probe and said proximal end of said dilation probe, a plurality of blades attached to project radially from said dilation probe; and moving said dilation probe of said device in the vessel and through the stenosis to incise and dilate the stenosis.

17. A method as recited in claim 16 wherein said catheter and said dilation probe are formed with a contiguous lumen and wherein said advancing step is accomplished by the steps of:

prepositioning a guidewire in the vessel and through the stenosis; and inserting said guidewire into said lumen; and advancing said dilation probe and said catheter over said guidewire and into contact with the stenosis.

18. A method as recited in claim 16 further comprising the steps of:

prepositioning a guide catheter in the vessel, said guide catheter being formed with a lumen for receiving said dilation probe and said catheter therethrough to guide said dilation probe to the stenosis; and Advancing said dilation probe and said catheter through said lumen of said guide catheter and into contact with the stenosis.

19. A method as recited in claim 16 wherein said device further comprises a selectively inflatable balloon mounted on said catheter proximal to said dilation probe, and said method further comprises the step of selectively inflating said balloon against the stenosis after the dilation probe has dilated and incised the stenosis.

20. A method as recited in claim 16 wherein said device further comprises means for rigidizing a portion of said catheter proximal to said dilation probe to facilitate movement of said dilation probe through the stenosis.

* * * * *